(12) United States Patent
Broberg et al.

(10) Patent No.: US 9,788,879 B2
(45) Date of Patent: Oct. 17, 2017

(54) PATELLA PROTECTOR

(71) Applicants: Mark Broberg, East Wenatchee, WA (US); Patrick Therien, Bothell, WA (US)

(72) Inventors: Mark Broberg, East Wenatchee, WA (US); Patrick Therien, Bothell, WA (US)

(*) Notice: Subject to any disclaimer, the term of this patent is extended or adjusted under 35 U.S.C. 154(b) by 400 days.

(21) Appl. No.: 14/698,044

(22) Filed: Apr. 28, 2015

(65) Prior Publication Data

US 2015/0305790 A1    Oct. 29, 2015

Related U.S. Application Data

(60) Provisional application No. 61/985,398, filed on Apr. 28, 2014.

(51) Int. Cl.
*A61B 17/88* (2006.01)

(52) U.S. Cl.
CPC .................. *A61B 17/8866* (2013.01)

(58) Field of Classification Search
CPC .................. A61B 17/064; A61B 17/8866
See application file for complete search history.

(56) References Cited

U.S. PATENT DOCUMENTS

2006/0241633 A1* 10/2006 Stalcup ............... A61B 17/025
606/86 R

* cited by examiner

*Primary Examiner* — Christian Sevilla
(74) *Attorney, Agent, or Firm* — James Haugen; Seattle Patent Group LLC

(57) ABSTRACT

A patella protector may be positioned in a manner in which it does not obstruct a patella or a prosthesis, while providing protection for the patella from accidental damage during a surgical procedure, such as a knee replacement. The patella protector may be a clamp with two contact surfaces connected by a stainless steel connecting element providing an inward bias to hold the contact surfaces against the patella.

7 Claims, 5 Drawing Sheets

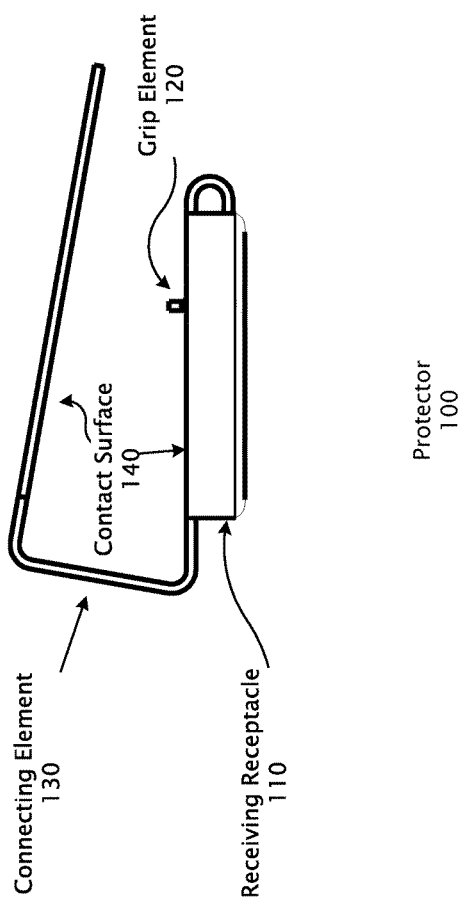

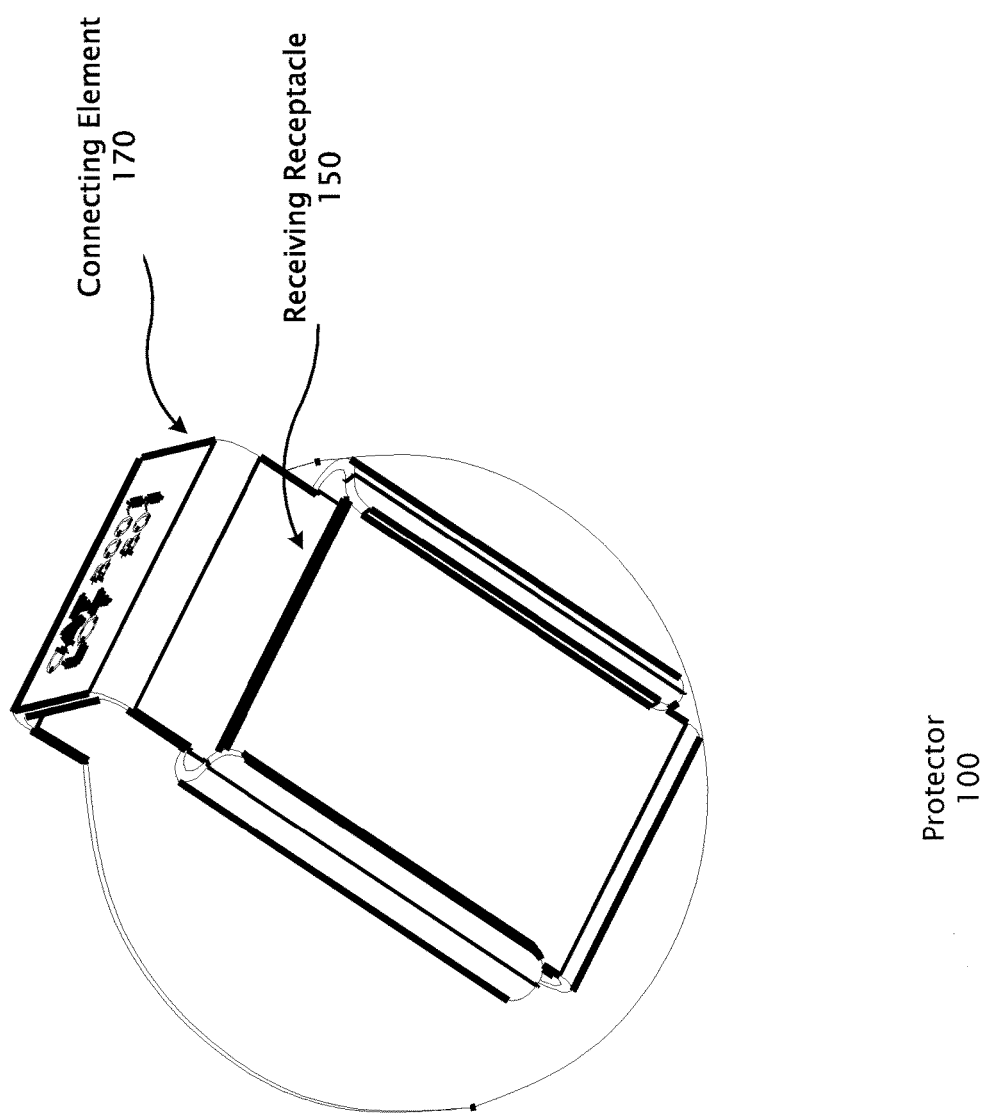

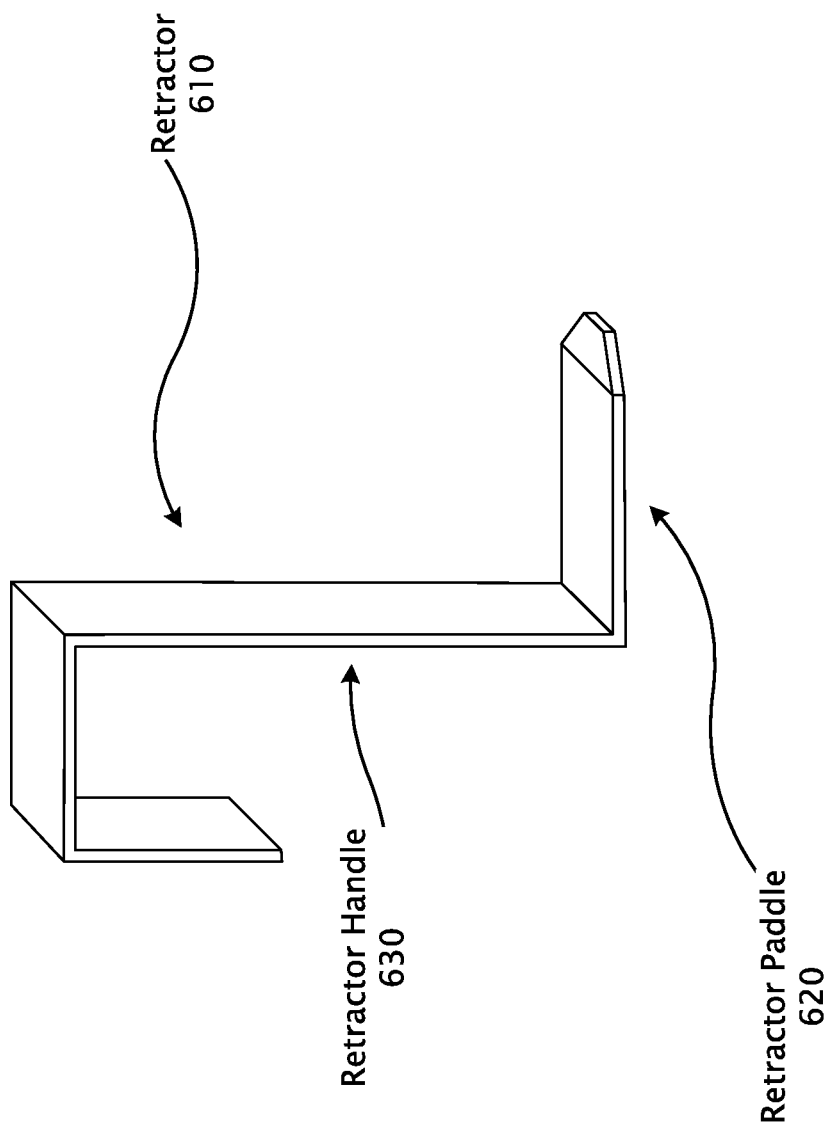

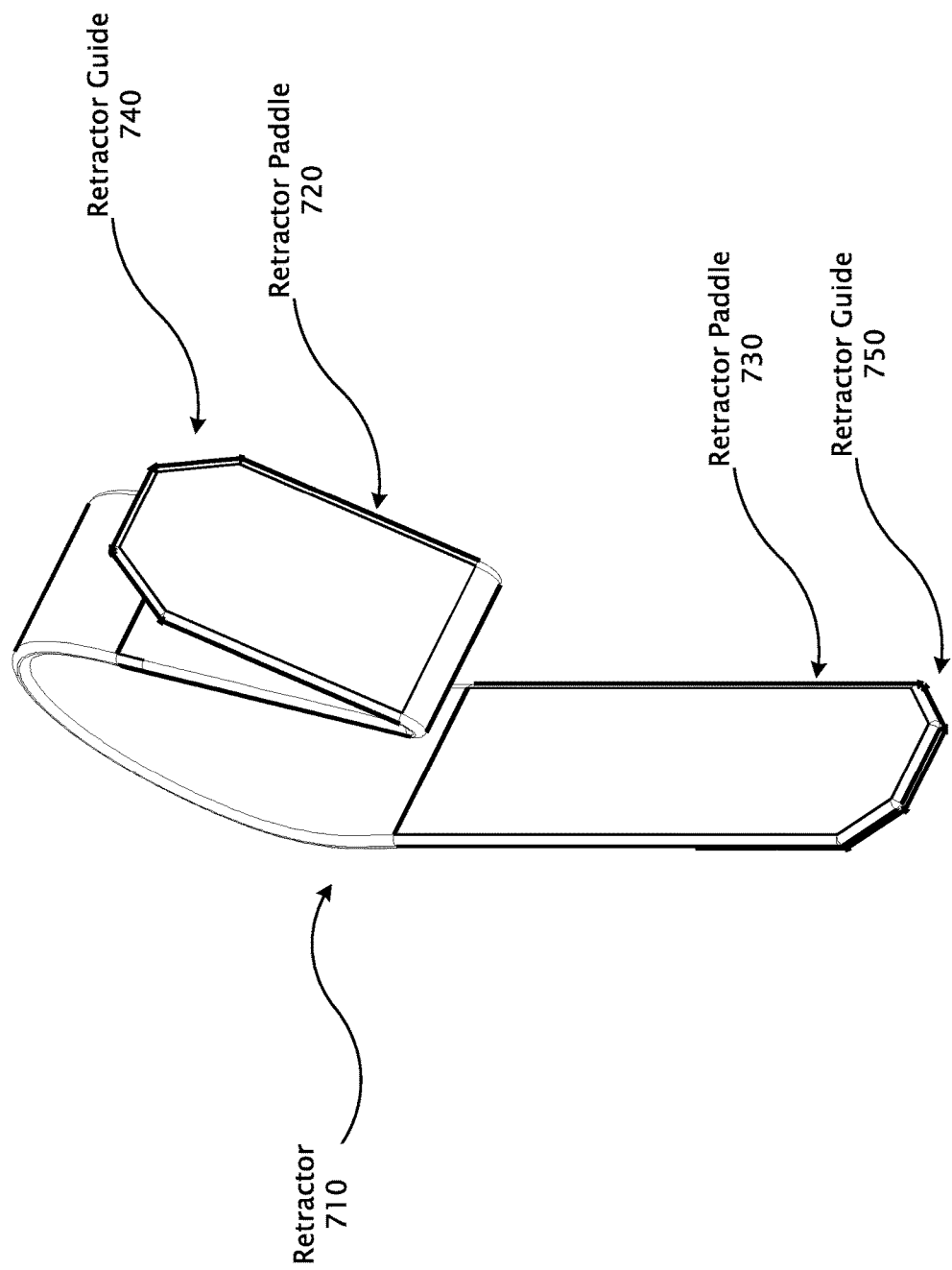

PATELLA PROTECTOR

FIELD

The instant application relates to a patella protector.

BACKGROUND

Total knee replacement procedures often require an orthopedic surgeon to bond a patella prosthesis to a patient's prepared patella using bone cement near the conclusion of the procedure. The patella prosthesis may be held in place during the time it takes the bonding cement to cure by a traditional non-modular medical instrument patella protector, for example a scissor type, that maintains compression by being held by the hand or by being compressed then locked in position. A bulky traditional patella protector may interfere with the rest or the procedure, and an orthopedic surgeon may have to wait and do nothing while the cement cures before completing the procedure. It may take ten minutes or longer for the cement to cure. In that situation, the total time for a full knee replacement may be extended, resulting in increased risk to the patient associated with being under anesthesia with an open wound, a constraint on the orthopedic surgeon's time and a waste of operating room resources.

SUMMARY

The instant application discloses, among other things, a patella protector. The patella protector may be a clamp configured to protect the prepared patella and patella prosthesis from damage during a procedure, such as a knee replacement. A patella protector may be helpful in other procedures by allowing a patella to be moved or retracted out of the way and protected. A retractor may also couple with a patella protector, which may permit additional control or ease of positioning and removal of the patella protector.

The patella protector may have one or more surfaces of sufficient size in contact with the prepared patella. The contact surfaces may have one or more grip elements to securely engage the patella prosthesis. The contact surfaces may be physically coupled by a connecting element that may produce an inwardly biased force between the contact surfaces, which may be sufficient to hold the patella protector in place during the procedure. The design of the patella protector may a grip element, which may provide a single point of contact on the prepared patella bone surface, which may allow free rotation while maintaining full compression. This may allow full rotational freedom and optimal placement of the patella protector for optimal protection. The patella protector may be discarded at the conclusion of the procedure, or may be reused.

BRIEF DESCRIPTION OF THE DRAWINGS

FIG. 2 is a side view of a patella protector according to one embodiment.

FIG. 3 is a bottom perspective view of a patella protector according to one embodiment.

FIG. 4 is a perspective view of a retractor, according to one embodiment.

FIG. 5 is a perspective view of a retractor, according to another embodiment.

DESCRIPTION

Figure 1:
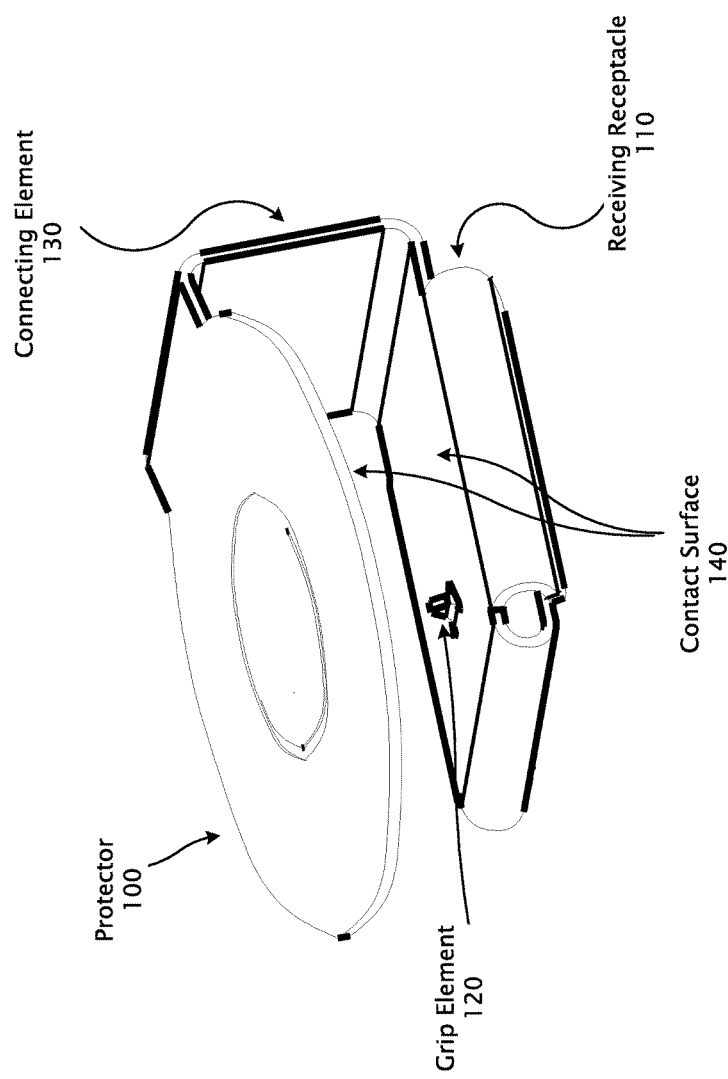
FIG. 1 is a perspective view of a patella protector according to one embodiment.

In one embodiment, a Patella Protector 100 may be used during a knee replacement procedure is completed. Once the procedure is completed, the patella protector may be removed using a retractor. The patella protector may have the benefit of protecting the patella implant while the surgeon completes the joint arthroplasty, for example, from any instruments or saw blades with which it may come in contact.

The patella protector may be designed to be applied by hand. A relatively small size of the patella protector may offer the surgeon the space and capability to continue working on the procedure while still protecting the patella. The nature of the patella protector may also allow it to be discarded at the end of the procedure.

Reference will now be made in detail to embodiments of the instant application, examples of which are illustrated in the accompanying drawings. Whenever possible, the same reference numbers will be used throughout the drawings to refer to the same or like parts.

Although discussed in reference to certain illustrations, the instant application is not limited to those illustrations.

FIG. 1 is a perspective view of Patella Protector 100 according to one embodiment. Patella Protector 100 may be used during, for example, knee replacement surgery, to protect a patella.

Patella Protector 100 may be constructed of a medical grade material or combination of materials. For example, Patella Protector may be made of glass filled high tensile strength plastics like acetal, polycarbonate, Ultem™ or similar plastics, stainless steel, carbon fiber, Kevlar®, other engineered resins, or minerals. In another embodiment, Patella Protector may have a Polytetrafluoroethylene (PTFE) or a superhydrophobic coating to shed blood and synovial fluid. One having skill in the art will recognize that Patella Protector may be made of other materials which are strong, lightweight, and autoclave tolerant. Patella Protector may have a plurality of Contact Surfaces 140. Contact Surfaces 140 may be coupled by Connecting Element 130. Connecting Element 130 may be constructed of a medical grade material, for example, stainless steel. Connecting Element 130 may produce an inwardly biased force between Contact Surfaces 140 sufficient to hold Patella Protector 100 in place during a procedure. One or more Contact Surface 140 may include Grip Element 120 to securely engage Patella Protector 100 to a prepared patella bone. Grip Element 120 may comprise a pointed projection from Contact Surface 140, and may allow free rotation about the patella bone while maintaining full compression.

Receiving Receptacle 110 may be configured to receive Retractor Paddle 620, Retractor Paddle 720, or another similar device, which may allow for easier or more accurate positioning of Patella Protector 100.

FIG. 2 is a side view of a patella protector according to one embodiment.

FIG. 3 is a bottom perspective view of a patella protector according to one embodiment.

FIG. 4 is a perspective view of Retractor 610, according to one embodiment. Retractor 610 may be a metal strip pre-bent to a convenient shape. Retractor Paddle 620 may be inserted into Receiving Receptacle 150 on Patella Protector 100 while Patella Protector 100 is coupled to a patella. Retractor 610 may help protect the patella during an operation, and may be used to simplify removal of Patella Protector 100 when Patella Protector 100 is no longer desired. Retractor 610 may act as a joystick to allow a surgeon or assistant to move or retract Patella Protector 100 during a procedure.

FIG. 5 is a perspective view of Retractor 710, according to another embodiment. Retractor 710 may be a metal strip pre-bent to a convenient shape. Either end of Retractor 710, Retractor Paddle 720 or Retractor Paddle 730, may be inserted into Receiving Receptacle 150 on Patella Protector 100 while Patella Protector 100 is coupled to a patella, which may allow flexibility in positioning for different aspects of a procedure. Retractor 710 may help protect the patella during an operation, and may be used to simplify removal of Patella protector 100 when it is no longer desired. Retractor 710 may act as a joystick to allow a surgeon or an assistant to move or retract Patella Protector 100 during a procedure.

Retractor Guide 740, 750 may simplify insertion of Retractor 710 into Receiving Receptacle 110, allowing slight variations of positioning of Retractor 710 to be self-correcting.

The illustrated operations in the description may show certain events occurring in a particular order. In alternative embodiments, certain operations may be performed in a different order, modified or removed. Moreover, steps may be added to the above-described logic and still conform to the described embodiments. Further, operations described herein may occur sequentially, or certain operations may be processed in parallel.

The foregoing description of various embodiments of the invention has been presented for the purposes of illustration and description. It is not intended to be exhaustive or to limit the invention to the precise form disclosed. It is intended that the scope of the invention be limited not by this detailed description, but rather by the claims appended hereto. The above specification, examples and data provide a complete description of the manufacture and use of the invention. Since many embodiments of the invention can be made without departing from the spirit and scope of the invention, the invention resides in the claims hereinafter appended.

The invention claimed is:

1. A patella protector, comprising:
   a clamp having a plurality of contact surfaces configured contact a patella to shield, move or retract a patella during a surgical procedure;
   a connecting element operable to couple at least two of the contact surfaces, the connecting element producing an inwardly biased force between the at least two of the contact surfaces;
   a receptacle operable to receive a removable retractor;
   at least part of the patella protector comprising a super hydrophobic coating; and
   wherein at least one of said contact surfaces has a grip element comprising a pointed projection configured to engage a patella, the grip element configured to allow rotation of the patella protector about an axis.

2. The patella protector of claim 1, further comprising a retractor operable to couple with the patella protector and provide additional control in positioning and removal of the patella protector.

3. The patella protector of claim 1, wherein the patella protector is constructed of a medical grade material.

4. The patella protector of claim 1, wherein the connecting, element is made of stainless steel.

5. The patella protector of claim 2, wherein the retractor comprises a metal strip.

6. The patella protector of claim 5, wherein the retractor is designed to be operable in two orientations.

7. The patella protector of claim 5, wherein the retractor comprises retractor guides.

* * * * *